United States Patent [19]

Oster et al.

[11] Patent Number: 5,019,496
[45] Date of Patent: May 28, 1991

[54] PHOTOPOLYMERIZATION DIAGNOSTIC TEST COMPOSITION AND METHOD FOR IMMUNOASSAY AND NUCLEIC ACID ASSAY

[76] Inventors: Gerald Oster, 241 W. 11th St., New York, N.Y. 10014; Baruch J. Davis, Mount Sinai Medical Center, 1 Gustave Levy Pl., New York, N.Y. 10029

[21] Appl. No.: 312,544

[22] Filed: Feb. 17, 1989

[51] Int. Cl.$^5$ .................. G01N 33/53; C12Q 1/68
[52] U.S. Cl. .................................... 435/6; 435/4; 435/71; 435/91; 436/501; 436/538; 436/37; 526/59; 526/123; 526/152; 526/171; 526/173; 526/240; 526/329.7; 526/341; 530/387; 536/27; 935/17; 935/88
[58] Field of Search ................... 435/4, 6, 7, 91; 436/501, 538, 37; 526/59, 123, 152, 171, 173, 240, 329.7, 341, 915, 918; 530/387; 536/27; 935/17, 88

[56] References Cited

U.S. PATENT DOCUMENTS 4,391,904 7/1983 Litman et al. .................. 435/7
4,711,840 12/1987 Nowinski et al. ............... 435/7
4,749,647 6/1988 Thomas et al. .................. 435/6

OTHER PUBLICATIONS

Oster et al. (1968) Chemical Reviews, vol. 68, No. 2, pp. 125-151.
Carrico, R. J., "Immunoassays Using Enzymic Cycling of Cofactor Labels", pp. 99-113; *Clinical Immunochemistry: Principles of Methods of Applications*, Eds. R. C. Boguslaski, E. T. Maggio, & R. M. Nakamura, (1984).
Morris, David L., "9 Apoenzyme Reactivation Immunoassays Using Flavin Adenine Dinucleotide as Label", pp. 115–130; *Clinical Immunochemistry: Principles of Methods and Applications*, Eds. Boguslaski et al, (1984).
Dainton: "Atoms and Radicals in Aqueous Media", *J. Chem. Soc.* Part 2:1533-1546, 1952.
Yang, N. L. & Oster, G., "Dye-Sensi. Photopoly. in the Presence of Rever. Oxygen Carriers", *J. of Phys. Chem.*, 74, 856 (1970).

*Primary Examiner*—Robert A. Wax
*Assistant Examiner*—Ardin H. Marschel
*Attorney, Agent, or Firm*—Sprung Horn Kramer & Woods

[57] ABSTRACT

A diagnostic test composition for detecting and measuring an analyte possessing biologic activity comprising
  (a) a photocatalyst system capable of converting a monomer to a polymer upon exposure to light, the monomer capable of undergoing addition polymerization, the photocatalyst system comprising one or more chemical moieties, with
     (1) the analyte comprising at least one such moiety or generating at least one such moiety or
     (2) in the case that the analyte lacks a photocatalyst property, the analyte is linked by a specific ligand to at least one such moiety or is linked by the specific ligand to a generator of at least one such moiety and
  (b) at least one monomer capable of undergoing addition polymerization.

40 Claims, No Drawings

PHOTOPOLYMERIZATION DIAGNOSTIC TEST COMPOSITION AND METHOD FOR IMMUNOASSAY AND NUCLEIC ACID ASSAY

BACKGROUND OF THE INVENTION

1. Field of the Invention

The present invention concerns the utilization of addition polymerization, e.g., vinyl polymerization, in diagnostic test compositions for detecting and measuring an analyte possessing biologic activity and in methods for detecting and measuring an analyte possessing biologic activity.

2. Background Information

Modern diagnostic tests for trace amount of analyte possessing biologic activity, such as those encountered in clinical laboratory medicine often employ immunologic (i.e., antigen-antibody) reactions.

Comparable techniques employing nucleic acid hybridization probes for the analysis of nuclei acids have entered the realm of clinic and research laboratories.

These highly specific reactions are detected by means of a label or tag, attached to one of the components, that is either chromophoric, fluorescent, radioactive, chemiluminescent or an enzyme that can generate such signals. Chromophore labels for detection of trace analytes are of historic and academic interest only because of their low sensitivity. Color detection methods are capable of detecting no fewer than $10^{18}$ to $10^{15}$ analyte molecules per milliliter, while radioisotope detection methods can approach a detection sensitivity in the range of $10^8$ to $10^7$ analyte molecules per milliliter.

Fluorescent chemiluminescent and enzymatic methods as characterized by relative-specific-activities can be more sensitive than radiosiotope methods by at least two or more magnitudes. These are goals, however, and not achievements. Continued increases in sensitivity are reported as these methods are refined, but no magnitude jumps are anticipated.

Prior to the present invention, no one proposed the coupling of an extraneous non-catalytic substance with a catalyst component of vinyl polymerization. If the extraneous substance is a highly specific ligand for a target analyte of interest, then the production of detectable polymer can indicate the presence and site of the analyte. This linkage provides the basis of a unique detection system. The present invention when applied to analytes of biologic interest provides a diagnostic technique useful in the fields of medicine and agriculture.

The present invention is designed to detect and measure the following types of analytes:

1. An analyte that possesses photocatalyst properties for the production of addition, e.g., vinyl, polymers;
2. an analyte that does not possess such photocatalyst properties, but forms a stable complex with a specific ligand, the latter capable of being linked to one or more moieties of such a catalyst system. Such analytes include, among others, immunoreactive substances and nucleic acids.

SUMMARY OF THE INVENTION

It is an object of the present invention to provide a sensitive method to detect and measure analytes possessing biologic activity, which method is economical and easy to use.

It is a further object of the present invention to provide a method to detect and measure such analytes in which a result can be obtained in a short amount of time.

The above objects and other objects, aims and advantages are satisfied by the present invention.

The present invention concerns a diagnostic test composition for detecting an analyte possessing biologic activity, the composition comprising (a) a photocatalyst system capable of converting a monomer to a polymer on exposure to light, said monomer capable of undergoing addition polymerization, the photocatalyst system comprising one or more chemical moieties with
  1. the analyte comprising at least one such moiety or generating at least one such moiety or
  2. in the case that the analyte lacks a photocatalyst property, the analyte is linked by a specific ligand to at least one such moiety or is linked by the specific ligand to a generator of at least one such moiety and (b) at least one monomer capable of undergoing addition polymerization.

The present invention further concerns a diagnostic immunoassay test composition wherein said specific ligand is selected from the group consisting of an antibody, an antigen binding segment of an antibody, an antigen and a hapten, wherein when the specific ligand is an antibody or an antigen binding segment of an antibody, the analyte is an antigen or a hapten and wherein when the specific ligand is an antigen or hapten, the analyte is an antibody or an antigen binding segment of an antibody.

The present invention further concerns a diagnostic test composition for the assay of a nucleic acid wherein said specific ligand is a hybridizable nucleic acid probe containing a known sequence, said sequence being single stranded and complementary to a single stranded segment of a nucleic acid analyte.

The present invention is further directed to a method for detecting an analyte that is a photosensitizer or an enzyme which generates a photosensitizer comprising (a) combining 1) the photosensitizer analyte or 2) the enzyme analyte that generates a photosensitizer from its precursor, the photosensitizer in the presence of an electron donor capable on exposure to light of converting a monomer to a polymer through addition polymerization, said monomer capable of undergoing addition polymerization, 3) an electron donor and 4) in the case of the enzyme a precursor of the photosensitizer together with 5) at least one monomer capable of undergoing addition polymerization, (b) exposing the resultant combination of (a) to light and (c) determining the extent of addition polymerization as an indicator of the presence and/or quantity of analyte.

The present invention is further directed to a method for detecting an analyte that is an electron donor or an enzyme that generates an electron donor comprising (a) combining 1) the electron donor analyte or 2) the enzyme analyte that generates an electron donor from its precursor, the electron donor capable of reducing a light excited photosensitizer, the photosensitizer capable of converting a monomer to a polymer through addition polymerization, said monomer capable of undergoing addition polymerization, 3) a photosensitizer and, 4) in the case of the enzyme, a precursor of the electron donor, together with 5) at least one monomer capable of undergoing addition polymerization,
(b) exposing the resultant combination of (a) to light and
(c) determining the extent of addition polymerization as an indicator of the presence and/or the quantity of analyte.

The present invention is further directed to a method for detecting an antibody or an antigen binding segment of an antibody comprising
(a) linking an antigen or a hapten to 1) a photosensitizer or 2) an enzyme that generates a photosensitizer from its precursor, the photosensitizer capable of converting a monomer capable of undergoing addition polymerization, e.g., a vinyl monomer or a vinylidine monomer, to a polymer, e.g., a vinyl polymer, on exposure to light,
(b) contacting the linked antigen or hapten with a complementary antibody or an antigen binding segment of an antibody in the presence of an electron donor and in the case of the enzyme, a precursor of a photosensitizer, together with at least one monomer capable of undergoing addition polymerization,
(c) exposing the resultant mass from (b) to light, and
(d) determining the extent of addition polymerization as an indicator of the presence and/or the quantity of the antibody or antigen binding segment of an antibody.

The present invention is still further directed to a method for detecting an antigen or a hapten comprising
(a) linking an antibody or an antigen binding segment of an antibody to (1) a photosensitizer or (2) an enzyme that generates a photosensitizer from its precursor, the photosensitizer in the presence of an electron donor capable of converting a monomer capable of undergoing addition polymerization, e.g., a vinyl monomer or a vinylidine monomer to a polymer e.g., a vinyl polymer, on exposure to light.
(b) contacting the linked antibody or an antigen binding segment of an antibody with a complementary antigen or hapten in the presence of an electron donor and in the case of the enzyme, a precursor of a photosensitizer together with at least one monomer capable of undergoing addition polymerization,
(c) exposing the resultant mass from (b) to light, and
(d) determining the extent of addition polymerization as an indicator of the presence and/or the quantity of the antigen or hapten.

The present invention is further directed to a method for detecting an antibody or an antigen binding segment of an antibody comprising
(a) linking an antigen or a hapten to (1) an electron donor or (2) an enzyme that generates an electron donor from its precursor, the electron donor being capable of reducing a light excited photosensitizer, the photosensitizer capable of converting a monomer capable of undergoing addition polymerization, e.g., a vinyl monomer or a vinylidine monomer, to a polymer, e.g., a vinyl polymer, on exposure to light,
(b) contacting the linked antigen or hapten with a complementary antibody or an antigen binding segment of an antibody in the presence of a photosensitizer and in the case of the enzyme, a precursor of an electron donor, together with at least one monomer capable of undergoing addition polymerization,
(c) exposing the resultant mass from (b) to light, and
(d) determining the extent of addition polymerization as an indicator of the presence and/or the quantity of the antibody or an antigen binding segment of an antibody.

The present invention is still further directed to a method for detecting an antigen or a hapten comprising
(a) linking an antibody or an antigen binding segment of an antibody to (1) an electron donor or (2) an enzyme that generates an electron donor from its precursor, the electron donor capable of reducing a light excited photosensitizer, the photosensitizer capable of converting a monomer capable of undergoing addition polymerization, e.g., a vinyl monomer or a vinylidine monomer to a polymer, e.g., a vinyl polymer, on exposure to light,
(b) contacting the linked antibody or an antigen binding segment of an antibody with a complementary antigen or hapten in the presence of a photosensitizer and in the case of the enzyme, a precursor of an electron donor together with at least one monomer capable of undergoing addition polymerization,
(c) exposing the resultant mass from (b) to light, and
(d) determining the extent of addition polymerization as an indicator of the presence and/or the quantity of the antigen or hapten.

The present invention is further directed to a method for detecting a nucleic acid comprising
(a) linking a hybridizable nucleic acid probe containing a known sequence, said sequence being single stranded and complementary to a single stranded segment of an analyte nucleic acid to 1) a photosensitizer or 2) an enzyme that generates a photosensitizer from its precursor, the photosensitizer capable of converting a monomer capable of undergoing addition polymerization, e.g., a vinyl monomer or a vinylidine monomer to a polymer, e.g., a vinyl polymer, on exposure to light,
(b) contacting the linked nucleic acid probe with the analyte nucleic acid in the presence of an electron donor and in the case of the enzyme, a precursor of a photosensitizer, together with at least one monomer capable of undergoing addition polymerization,
(c) exposing the resultant mass from (b) to light and
(d) determining the extent of addition polymerization as an indicator of the presence of and/or the quantity of nucleic acid analyte.

The present invention is still further directed to a method for detecting a nucleic acid comprising
(a) linking a hybridizable nucleic acid probe containing a known sequence, said sequence being single stranded and complementary to a single stranded segment of an analyte nucleic acid to 1) an electron donor or 2) an enzyme that generates an electron donor from its precursor, the electron donor being capable of reducing a light excited photosensitizer, the photosensitizer capable of converting a monomer capable of undergoing addition polymerization, e.g., a vinyl monomer or a vinylidene monomer, to a polymer, e.g., a vinyl polymer, on exposure to light,
(b) contacting the linked nucleic acid probe with the analyte nucleic acid in the presence of a photosensitizer and in the case of an enzyme, a precursor of an electron donor, together with at least one monomer capable of undergoing addition polymerization, (c) exposing the resultant mass from (b) to light, and (d) determining the extent of addition polymerization as an indicator of the presence and/or the quantity of nucleic acid analyte.

The present invention is also directed to a method for detecting a nucleic acid analyte comprising (a) contacting a hybridizable nucleic acid probe containing a known sequence, said sequence being single stranded and complementary to a single stranded segment of nucleic acid analyte with said analyte, (b) linking the probe to 1) a photosensitizer or 2) to an enzyme that generates a photosensitizer from its precursor, the photosensitizer capable of converting a monomer capable of undergoing addition polymerization, e.g., a vinyl monomer or a vinylidine monomer, to a polymer, e.g., a vinyl polymer, on exposure to light, in the presence of an electron donor and in the case of an enzyme, a precursor of a photosensitizer, together with at least one monomer capable of undergoing addition polymerization, (c) exposing the resultant mass from (b) to light and (d) determining the extent of addition polymerization as an indicator of the presence and/or quantity of nucleic acid analyte.

The present invention is also directed to a method for detecting a nucleic acid analyte comprising (a) contacting a hybridizable nucleic acid probe containing a known sequence, said sequence being single stranded and complementary to a single stranded segment of a nucleic acid analyte, with said analyte, (b) linking the probe to 1) an electron donor or 2) to an enzyme that generates an electron donor from a precursor, the electron donor being capable of reducing a light excited photosensitizer, the photosensitizer capable of converting a monomer capable of undergoing addition polymerization, e.g., a vinyl monomer or a vinylidine monomer, to a polymer, e.g., a vinyl polymer, on exposure to light, in the presence of a photosensitizer and, in the case of an enzyme, a precursor of an electron donor, together with at least one monomer capable of undergoing addition polymerization, (c) exposing the resultant mass from (b) to light, and (d) determining the extent of addition polymerization as an indicator of the presence and/or quantity of nucleic acid analyte.

In contrast to the aforesaid heretofore employed efforts to refine well established methods, the present invention provides additional amplification factors inherent in the catalytic and chain reaction nature of addition (vinyl) polymerization. The potential sensitivity is exceedingly high for the following reasons:

(1) The photosensitizer of a photocatalyst system for vinyl polymerization can be recycled indefinitely in the presence of an electron donor source that protects the photosensitizer from undergoing irreversible photooxidation. Each cycle of photoreduction yields a free radical capable of initiating chain polymerization.

(2) The photosensitizer and/or the electron donor can be generated by an enzyme-labeled analyte. Horseradish peroxidase is one such enzyme.

(3) A single free radical molecule can initiate the formation of a polymer chain molecule composed of $10^5$ to $10^6$ monomer molecule units. A particle visible to the naked eye under light scattering conditions can be the product of as few as 2 to 4 free radical molecules.

A crude indication of the sensitivity of the present invention is provided by a simple procedure in which one microliter samples of solution of Thionin dye of diminishing concentration are spotted and dried on a glass microscope slide, each spot about 2mm in diameter. The slide is then immersed in an aqueous solution of barium acrylate and electron donor, nitrogen gas is bubbled through for several minutes to reduce the oxygen concentration, and the slide and container is exposed to a filtered 250 Watt incandescent lamp at 5cm for 2 to 3 minutes. At the end of this time white opaque 2mm diameter discs of barium polyacrylate are grossly visible at the sites containing about $10^8$ to $10^7$ dye molecules.

The present invention is applicable to virtually all immunoassay techniques and nucleic acid hybridization techniques and thereby renders such techniques considerably more sensitive and convenient than the conventional techniques discussed hereinabove. The present invention is directly applicable to enzyme linked assays, including the well established peroxidase assays. Horse radish peroxidase, with its known high turnover rate (5 million hydrogen peroxide molecules converted per enzyme molecule per minute), can by the present invention catalyze addition polymerization, e.g., vinyl polymerization, via the generation of a photosensitizer.

DETAILED DESCRIPTION OF THE INVENTION

The present invention concerns a diagnostic test which comprises a chemical composition which contains one or more test substances of biologic interest. The composition in the presence of the analyte undergoes addition polymerization, e.g., vinyl polymerization, to yield a measurable amount of polymer. More specifically, the composition contains (a) a photocatalyst system designed to convert monomer to polymer and (b) one or more monomers, e.g., vinyl monomers or vinylidine monomers, capable of undergoing polymerization in the presence of free radicals.

The photocatalyst system comprises a photosensitizer or an enzyme that generates such a photosensitizer and one or more electron donors or an enzyme that generates an electron donor.

A specific ligand for an analyte is linked to one or more chemical moieties of the photocatalyst system. The ligand is the portion of the complex that makes contact with a target analyte and confers specificity and provides a bridge connecting the analyte with a photocatalyst or a generator of such a moiety.

The test substances (analytes) are comprised of two classes:

(a) the analyte is a photosensitizer or an enzyme that generates a photosensitizer or an electron donor or an enzyme that generates an electron donor;

(b) the analyte lacks photocatalyst properties, but is capable of forming a stable complex with a specific ligand that is capable of being linked to a photosensitizer moiety or to a generator (enzyme) of such a moiety or to an electron donor or to a generator (enzyme) of such a moiety.

The class of analytes possessing photocatalyst system properties or capable of generating such moieties is comparatively small, but includes members of considerable biologic interest. Riboflavin, porphyrins, reduced nicotinamide adenine dinucleotide (NAD) and reduced nicotinamide adenine dinucleotide diphosphate (NADP) are photosensitizers; the latter two can also serve as electron donors. Hydrolytic enzymes such as esterase can generate photosensitizers from, for example, the esters of coumarin and fluorescein derivatives. NAD and NADP oxidoreductase enzymes can generate reduced NAD and NADP.

The second class of analytes, those lacking photocatalyst properties, but capable of forming stable complexes with their specific ligands, is a very numerous class comprised of two large groups, immunoreactive analytes and nucleic acid analytes and smaller groups such as lectins, messengers, specific cell surface receptors, gene regulating proteins, haptoglobins, etc.

In the case of an immunoassay, the specific ligand and its target analyte are the elements that combine to form the immune complex common to all immunoassay procedures. These include the immunoglobulin antibodies, antibody segments that contain the complementary site, antigens and haptens. As is also evident, either element of the complex can serve as the specific ligand for the detection of the other, the analyte.

In the case of nucleic acid assay by means a hybridizable probe the analyte is deoxyribose nucleic acid (DNA), ribose nucleic acid (RNA) or a polynucleotide portion of a nucleic acid whose complementary portion for hybridization is in a single strand state.

Since with few exceptions the specific ligands for assay of immunoreactive substances and nucleic acids do not possess photocatalytic properties the ligand, either before or after it has formed its specific complex with the target analyte, must be bound to a moiety or a generator of a moiety of the photocatalyst system. The types of linkages and intermediate linking molecules are well known in the art and are applicable to both immunoassay and nucleic acid assay. For example, if a drug can be rendered immunogenic, the antibody that it evokes serves as the specific ligand that provides the necessary linkage; by coupling a photosensitizer or a photosensitizer generator (an enzyme) or an electron donor or an electron donor generator (i.e., an enzyme) to the antibody a reagent is formed which binds specifically to the drug and initiates polymer formation. Multiple combinations of intermediate linkages as presently utilized in immuno-diagnostic and nucleic acid assay techniques are equally applicable to the present invention. Thus, peroxidase enzyme can be coupled to avidin and the antigen of an antibody or the nucleic acid probe coupled to biotin so that in this particular linkage system the enzyme is the generator of a photosensitizer and the antibody and the nucleic acid the respective analytes. Here the enzyme is linked to the antibody or to the nucleic acid through a biotin-avidin complex, which once formed is essentially non-dissociable. Alternative linkages through antibodies to avidin, antibodies to biotin, and through Protein A can, for example, be utilized for both assays.

Further sensitivity can be gained by joining multiple photocatalyst moieties to a natural or synthetic polymer which in turn is linked to the specific ligand. If the molecule carrying the catalyst moiety is such a polymer or is an enzyme its bulkiness may impede the complexation of the ligand with the analyte. This problem can be obviated by first complexing the ligand and the analyte, then linking the ligand to the photocatalyst element.

In the present invention on causing the polymerization to occur, the polymer is thereby produced at the site of the analyte. In general, wherever in a biological specimen a photocatalyst moiety is bound (covalently or otherwise), then by the present invention the polymer will be produced at that site.

Further, the present invention is applicable at the microscopic level permitting the detection and localization of the analyte at the histochemical and cytochemical levels (e.g., tissue sections, individual cells and microorganisms).

In the present invention the preferred catalyst system for initiating addition polymerization operates through a free radical mechanism. The catalyst system requires light for its action. The light radiation supplies the energy to render reducible the light excited moiety (the photosensitizer) by an electron donor.

By the term photosensitizer is meant a substance which in the presence of an appropriate electron donor and under the action of light produces free radicals which are capable of initiating addition, e.g., vinyl polymerization.

In the present invention, an electron donor is defined as a substance which donates electrons, i.e., reduces a light excited photosensitizer. In the absence of light, however, the electron donor is incapable of reducing the photosensitizer.

The electron donor must be present in order to generate the initiator, a free radical, for addition polymerization, e.g., vinyl polymerization. In the present invention the photosensitizer in the presence of an electron donor is recycled and hence the initiation of addition polymerization, e.g., vinyl polymerization, is efficient. Because of this continuous recycling of the photosensitizer, only traces are required for polymerization. Conversely, when the analyte is linked to an appropriate electron donor, that is, one whose oxidation state is reversible, or linked to a generator of such a donor, there is a continuous recycling of the electron donor and only traces are required for polymerization.

Alternative catalyst systems employing ionic mechanisms for addition polymerization are also applicable in this invention.

In the present invention, the photosensitizers for free radical photopolymerization of the monomers include the following classes: flavins, coumarins, xanthenes, acridines and phenothiazines. The precursors which are converted into photosensitizers by enzymes include the following derivatives of the aforementioned photosensitizers; the acetates, the higher esters, phosphates, peptides, sulfates, glucuronates, galactosides and dihydro derivatives.

Non-limiting examples of coumarins for use in the present invention include amino coumarins and hydroxy coumarins, examples of which are as follows: 7-amino-4 methyl coumarin, 7-amino-4 trifluoromethy coumarin and 7-hydroxy-4-methyl coumarin and 7-hydroxycoumarin.

Non-limiting examples of acridine for use in the present invention include mono- and diaminoacridines such as the following: Acridine Yellow, Coriphosphine O, Acriflavine, Euflavine, Proflavine, Phosphine and Rheonine A.

Non-limiting examples of xanthenes for use in the present invention include Fluorescein and Fluorescein derivatives such as the following: Fluorescein, Eosin, dichlorofluorescein, Rose Bengal and dibromo eosin. Other xanthenes include members of the pyronine and rhodamine families.

Non-limiting examples of phenothiazines for use in the present invention include monoamino and diamino phenothiazines such as the following: Thionin, Azure C, Azure A, Toluidine Blue O, Methylene Blue, Methylene Green and New Methylene Blue.

Non-limiting examples of generators (enzymes) of the photosensitizer of the present invention include a peroxidase enzyme, a hydrolase enzyme and an oxidase enzyme.

Non-limiting examples of peroxidase enzymes for use in the present invention include the following: horseradish peroxidase, myeloperoxidase, thyroid peroxidase, salivary peroxidase, intestinal peroxidase, lactoperoxidase and microperoxidase.

The peroxidase can generate a photosensitizer selected from the non-limiting group consisting of a reduced xanthene and a reduced phenothiazine The reduced xanthene can be selected from the following group: fluorescin and its halogenated derivatives, non-limiting examples of which include dichlorofluorescin and dihydroeosin.

Oxidase enzymes that generate hydrogen peroxide provide, thereby the oxidant for peroxidase generation of a photosensitizer from the precursor. Non-limiting examples of such oxidase enzymes for use in the present invention include the following: alcohol oxidase, ascorbate oxidase, choline oxidase, galactose oxidase, glucose oxidase, oxalate oxidase, pyruvate oxidase and xanthine oxidase.

The hydrolase enzyme can be selected from the following non-limiting group: an esterase, lipase, sulfatase, glucuronidase, galactosidase, phosphatase or a peptidase.

The esterase and lipase can generate a photosensitizer selected from esters of Fluorescein and their halogenated derivatives, e.g., dichlorofluorescein and the acetates of 7-hydroxycoumarins.

The phosphatase can generate a photosensitizer selected from the diphosphate of Fluorescein and its halogenated derivatives, e.g., dichlorofluorescein diphosphate and phosphates of 7-hydroxycoumarins.

The peptidase can generate a photosensitizer from a peptide derivative of Thionin and Thionin derivatives.

In the instance when the analyte is linked to the photosensitizer or the generator of the photosensitizer the most effective non-limiting examples of electron donors are the following: triethanol amine, BISTRIS (bis[2-hydroxy-ethyl] imino tris [hydroxymethyl] methane), N-phenylglycine, BES (N,N-bis[2-hydroxymethyl]-2-amino-ethane sulfonic acid), BICINE (N,N-bis[2-hydroxyethyl]-glycine), TRICINE (N-tris hydroxymethyl] methyl glycine), HEPES (N-2-hydroxyethyl piperazine-N'-2-ethane sulfonic acid), TAPS (tris hydroxymethyl] methylaminopropane sulfonic acid), PIPES]) (piperazine-N, N'-bis [2-ethane sulfonic acid, MOPS (3-[N-morpholine] propane sulfonic acid), MOPSO (3-[N-morpholine]-2-hydroxypropane sulfonic acid), ADA (N-[2-acetamido]-2-iminodiacetic acid), AMPSO (N-[1,1-dimethyl-2-hydroxyethyl]-3-amino-2-hydroxypropane sulfonic acid), DIPSO (N,N-bis[2-hydroxyethyl]-3-amino-2-hydroxypropane sulfonic acid), EPPS (N-[2-hydroxyethyl] piperazine N'-3-propane sulfonic acid), HEPPSO (4-[2-hydroxyethyl] piperazine-1-[2-hydroxypropane sulfonic acid]), 2-morpholinoethanol, POPSO (piperazine-1,4 bis {2-hydroxypropane sulfonic acid]), MES (2-morpholinoethane sulfonic acid).

Also included are EDTA (ethylenediaminetetracetic acid), TEMED (tetramethylethylenediamine), triethylenetetramine, acetylacetone, 5,5-dimethyl-1-3-cyclohexanedione, dihydroxy fumaric acid, paratoluene-sulfinic acid, dithioerythritol, cysteine, reduced glutathione, nicotinamide adenine dinucleotide (NAD) and nicotinamide adenine dinucleotide phosphate (NADP). Also effective as electron donors in the present invention are salts of transition metals in their lower valence state, such as cobaltous, manganous, cuprous, cerous, nickelous, molybdenum and ferrous.

Electron donor generators according to the invention include the following oxidoreductase enzymes: nicotinamide adenine dinucleotide oxidoreductase, nicotinamide adenine dinucleotide phosphate oxidoreductase, cytochrome oxidoreductase and ferredoxin oxidoreductase.

It has been found that combinations of two or more electron donors are more effective than single donors. Most effective are combinations comprising a tertiary amine, a beta diketone and a salt of a transition metal.

In the instance when the ligand-analyte is linked to the electron donor moiety of the photocatalyst system, the photosensitizer is selected from the group listed above. The number and variety of electron donors, however, are more limited than those for the photosensitizer-linked ligand-analyte, since satisfactory detection sensitivity requires recycling of the donor (many otherwise useful electron donors undergo irreversible oxidation during photocatalysis). Both nicotinamide adenine dinucleotide (NAD) and nicotinamide adenine dinucleotide phosphate (NADP) can be cycled between oxidation states and both can function as electron donors for photoreduction of the light excited photosensitizer. R.J. Carrico ("Immunoassays Using Enzymic Cycling of Cofactor", *Clinical Immunochemistry: Principles of Methods and Applications*, Eds. R.C. Boguslaski, E.T. Maggio and R.M. Nakamura, pp. 99–114, Little Brown and Company, Boston/Toronto (1984)) reported hapten linked NADH (reduced NAD) capable of recycling in a homogeneous immunoassay in which the product is a reduced tetrazolium derivative. The preferred cyclable electron donors for use in the present invention (non-limiting) include: NAD, NADP, riboflavin, flavin adenine dinucleotide (FAD), flavin mononucleotide (FMN), ferricytochrome, ferredoxin, sulfhydryl compounds, methyl viologen and its derivatives.

In the instance when the ligand-analyte is linked to the generator of the electron donor, one of the above listed photosensitizers can be used. Generators of electron donors are the enzymes found in the class "oxidoreductase" and comprising the subclasses: NAD oxidoreductase, NADP oxidoreductase, ferricytochrome oxidoreductase and ferredoxin oxidoreductase (in the trivial nomenclature they are identified as "dehydrogenase" and "reductase" enzymes). Glucose-6-phosphate dehydrogenase, alcohol dehydrogenase, lactate dehydrogenase and glucose dehydrogenase are a few of the better known members.

Addition polymerization of vinyl monomers is a chain reaction whereby a single initiator molecule (typically a free radical) may cause the consecutive conversion of thousands, or even millions, of monomer units to form a high molecular weight polymer molecule. Although the process of polymerization of vinyl monomers is widely practiced in industry to yield such useful plastics as polystyrene, polymethyl methacrylate, polyacrylonitrile, and the like, the process has not heretofore been used as an indicator of trace amounts of biologic substances. Aside from the sensitivity of the reaction, its result is readily observed and easily measured. High molecular weight polymers are characterized by the fact that their physical properties are markedly different from those of the parent monomer. Thus acrylamide, for example, is soluble in methanol, but polyacrylamide is insoluble in methanol; acrylonitrile is water soluble (to the extent of 7 percent), but polyacrylonitrile is water insoluble; calcium acrylate is soluble in water, but polycalcium acrylate being a highly crosslinked polymer forms a second phase in water and so on. Thus these polymers are recognized in an appropriate solvent by the white light scattering mass which they form when polymerization of the monomer ensues. Many high polymers even in solvents which do not precipitate the polymers differ from the parent monomer in that they are tacky or sticky, whereas the monomer is not. Thus aqueous solution of such polymers as polyacrylamide and polymethacrylic acid form sticky highly viscous, colorless solutions which can plug up porous sieves, whereas the aqueous solutions of the monomer are nonviscous. Thus the production of even a small quantity of high polymer is readily observable and measurable.

The following monomers among others can be employed singularly or in combination in the present invention: acrylamide, N-octyl acrylamide, methacrylamide, N-methylacrylamide, acrylic acid, methacrylic acid, hydroxymethyl acrylamide, methylene bisacrylamide, acrylonitrile, methyl acrylate (and higher esters), ethylene glycol methacrylate, propylene glycol methacrylate, acrylamido propane sulfonic acid, vinyl pyrrolidone, vinyl pyridine, and the multivalent salts of acrylic and methacrylic acids, including calcium, barium, strontium, cadmium, neodymium, uranium and europium. Still further, preformed, synthetic and natural polymers to which vinyl groups can be coupled and which are capable of forming addition polymers can be used.

The intended method of detection of the polymer would usually be determined from the choice of the monomer. The most obviously visible polymer is that where dense crosslinks are produced, that is, where the monomer is polyfunctional, e.g., difunctional. Methylene bisacrylamide is one such monomer. The most versatile monomers are the divalent metal salts of acrylic acid. Many of the very sensitive systems of the present invention use calcium or barium acrylate. Barium acrylate might be effective for electron microscopy. Not only would the resolution be high because the polymer would remain restricted to the place where the photosensitive substance is produced, but also the polymer is relatively dense toward the penetration of electrons. Hence very thin samples of only a few Angstroms should show high contrast. Even more effective is uranium acrylate. Uranium (II) salts are fluorescent so the polymer would fluoresce under the action of near ultraviolet light. The fluorescence would be particularly intense because each monomer unit is the polymer fluorescent. A more effective monomer is europium (II) acrylate. Here the europium polyacrylate can be further processed to yield another europium chelate which emits red light (maximum 615 nm) when excited by 365 nm radiation. Red fluorescence can be measured with high precision in biological specimens because the background fluorescence is negligible.

There are a number of auxiliary techniques which further enhance the sensitivity and convenience of the present invention. For example, if the monomer is acrylamide the resultant polymer is sticky and will trap or entrain pigment granules thereby acquiring a color of high tinctorial power. Other types of granules which enhance the detection of the polymer include reflecting metals (e.g., aluminium powder), phosphorescent pigments (e.g., doped cadmium sulfide), or magnetic pigments for magnetic readout. Still further, soluble or particulate reagents entrained in the growing polymer or trapped on the surface of the polymer can serve as initiators of a second stage cascade that can, for example, generate additional polymer or a dye product.

Agglutination of a suspension of latex particles can be a very sensitive measure of vinyl polymerization. The polymer, unlike the monomer, could adhere to the latex particle causing a clumping of the particles.

The choice of light source for initiating polymerization will be determined by the particular sensitizer which is employed. Thus for 7-hydroxycoumarin near-ultraviolet light should be employed. Typically one uses a medium or high pressure mercury lamp because it is rich in the 365 nm line. When the photosensitizer absorbs blue light as is the case of dichlorofluorescein, for example, it is well to eliminate, with a blue filter, all the ultraviolet light and thereby eliminate effects which might cause the polymerization by the presence of impurities, which act as ultraviolet photosensitizers. Even better are blue colored dyes (and therefore red light absorbing) as photosensitizers. Such dyes include members of the phenothiazine family of dyes such as thionin and methylene blue. Here the light source can be a tungsten lamp. Even a chemiluminescent solution can serve as a source for photopolymerization.

The photochemical step may be shortened to a millisecond period by the use of a photographic flash lamp as the light source. In extremely viscous media the reaction proceeds even after the illumination is completed.

The photochemical step in the present invention can also be activated by a laser with spectral output corresponding to the absorption spectrum of the photosensitizer in question. Thus the helium neon laser is effective for Methylene Blue. If the dye is Eosin the green line of the copper laser is effective. The dye 2,7 dichlorofluorescein, calls for the blue argon laser line. For 7-hydroxycoumarin the effective ultraviolet radiation is obtained from quantum doubling of a visible laser or from a quantum quadrupling of an infrared laser. Since a laser beam can be focused to a spot of the diameter of the wavelength of the radiation, by the present invention a polymer can be produced in a small area.

The sensitivity and rapidity of detection of immunological reactions or of nucleic acid hybridizations using the present invention make practicable the efficient and economical search for the quantitation of possible interactions of a given test species with a very large number of substrates or complimentary species. The present invention also provides a means of performing automatic rapid screening of very large arrays of substances as is desired for analysis of gene compositions. Such arrays might include arrays of nucleic acids and their subunits and proteins and their subunits as encountered in the universe of immune phenomena or nucleic hybridization.

In photopolymerization, oxygen is a participant in the reaction. Too much oxygen, however, retards vinyl polymerization as is well known in the art. To reduce the induction period (and hence a delay in onset) in polymerization, a momentary flushing of the system with nitrogen gas is commonly performed to achieve, at least transiently, an approach to optimal conditions. A sustained optimal concentration should make for maximal performance. This is achieved in the present invention by means of an oxygen buffer. Cobalt chelates such as glycylglycine, histidine, diethylenetetramine, triethylenetetramine and vitamin B $_{12a}$, are suitable in the alkaline range (N.L. Yang and G. Oster, *J. Physical Chem.*; 74, 856 (1970)); oxidase enzymes such as alcohol oxidase, ascorbate oxidase, amino acid oxidases, xanthine oxidase, galactose oxidase, glucose oxidase, sarcosine oxidase, pyruvate oxidase and choline oxidase are suitable in the neutral pH range.

The examples given below are representative of the present invention and are not meant to limit the invention.

EXAMPLE 1: Non-Enzymatic Immunoassay

A. A fluoresceinated antibody is allowed to combine with its antigen which is first spotted and fixed on a glass slide. The uncombined antibody is washed off. The slide is dipped into a solution containing 15% barium acrylate and electron donors. On illumination with a tungsten iodine 50 watt lamp, a visible white polymer is produced at the site of the antigen.

B. The fluoresceinated antibody is replaced by a Toluidine Blue O coupled antibody and a similar result is obtained C. The above example A is repeated, using uranium acrylate instead of barium acrylate and the amount of antigen used is one-thousandth of that above.

After brief exposure to light, no polymer is visible but on examination with a mineralogists (Woods 365 nm) lamp a fluorescent polymer is seen at the site of the antigen. The control site of untreated antigen is negative. Another control where an antigen is treated with albumin is also negative.

In all of the above instances, the effects are more pronounced if sample is treated with nitrogen prior to illumination.

EXAMPLE 2: Non-Enzymatic Immunoassay

A. Thionin is coupled to avidin by means of the bifunctional linking agent, glutaraldehyde. A biotinylated antibody is employed to detect its antigen adsorbed on to the walls of a polystyrene well. Uncombined antibody is washed away. Next the well is treated with thioninated avidin and after incubation, the uncombined thioninated avidin is washed away. To the well is added a solution of 10% acrylamide with the electron donor pairs 0.5% triethanolamine and 0.5% acetylacetone. The system is illuminated with a 125 milliwatt Helium-Neon laser. After the removal of supernatant solution the well is washed with a carbon black suspension revealing a tacky polymer (to which carbon black granules adhere) at the site of the coupled antigen.

B. The same experiment is repeated using in place of the original electron donor pair each of the following electron donor pairs:
1% triethanolamine and 0.5% cobaltous chloride
1% triethanolamine and 0.05% manganous sulfate
1% triethanolamine and 0.05% cupric sulfate
1% triethanolamine and cerous chloride
5% nitrilotris propionamide and 0.5% acetylacetone
0.5% BisTris and 0.5% acetylacetone and similar results are obtained.

C. The same result is obtained by replacing thionin by the other listed phenothiazines. In place of thionin-avidin conjugate a thionin-biotin antibody conjugate is used and the same result is achieved. This provides an alternative means of performing the immunoassay.

The laser is replaced with a photographic flash lamp and the same results are obtained with a single flash.

In all of the above instances the effects are more pronounced if sample is treated with nitrogen prior to illumination.

EXAMPLE 3: Non-Enzymatic Immunoassay

In those instances where antigen-antibody reactions form insoluble complexes, the complex will have an affinity for anionic dyes, especially those of high polarizability like Rose Bengal (tetraiodotetrachloro fluorescein). Rose Bengal is a photosensitizer.

Fixed amounts of antigen and 10-3 molar Rose Bengal are added to a series of glass test tubes. To these tubes are added serial dilutions of antibody. The tubes are incubated for a fixed time and then centrifuged to carry down products of a immune reaction and the supernantants are removed. The pellets are resuspended in the 30% acrylamide, 0.5% triethanolamine and 0.5% acetylacetone and the sample tubes exposed to a 50 watt tungsten iodine lamp. After brief exposure the solutions are tested for polymer by pouring into methanol and the amount of polyacrylamide precipitate is noted. The polymer is indicative of the formation of insoluble antibody-antigen complexes. The tube with the greatest amount of polymer is also the sample where the combining proportions of the antibody-antigen are optimal and hence the analyte is titered.

EXAMPLE 4: Enzymatic Immunoassay

A. Dichlorodiacetyl fluorescin (DCDAF) is known to become fluorescent after hydrolysis (by alkali or by esterase enzyme) and subsequent treatment with peroxidase enzyme in the presence of hydrogen peroxide. What was not appreciated, as in the present invention, is that the final product, dichloro fluorescein can serve as a photosensitizer for the polymerization of vinyl monomers.

A peroxidase coupled antibody is allowed to combine with its antigen which is spotted and fixed on a glass slide. The uncombined antibody is washed off. The glass slide is immersed in a $10^{-4}$ molar solution of DCDAF, 0.001% esterase enzyme, 0.03% hydrogen peroxide, 15% calcium acrylate, 0.5% triethanolamine and 0.1% cerous chloride and is exposed to 250 watt medium pressure mercury lamp filtered with a cobalt blue glass filter. An adherent white precipitate of polymer forms at the site of the antigen.

B. In this example, glucose oxidase, conjugated to the antibody, and 5% glucose provide a source of hydrogen peroxide for the peroxidase which is now in free solution. The same result as in Example 4A is obtained.

EXAMPLE 5: Enzymatic Immunoassay

A. Porcine liver esterase coupled antigen is allowed to combine with its antibody spotted on a glass slide. The uncombined antigen is washed off. The slide is dipped into a solution containing $10^4$ molar fluorescein diacetate, 30% calcium acrylate and electron donors. On de-oxygenating by bubbling nitrogen and then illuminating the solution with a 150 watt Xenon-Mercury lamp with a glass ultraviolet cut off filter, a visible white polymer precipitates at the site of the antibody.

B. The de-oxygenating step using nitrogen is replaced by adding to the monomer solutions glucose oxidase (0.001%) and 8% glucose and incubating 10 minutes prior to exposure. A similar result is obtained.

In the above deoxygenating steps employing glucose oxidase, the glucose oxidase-glucose system is replaced by the dioxygenase enzymes and their substrates: a) ascorbic acid oxidase-ascorbic acid or by b) xanthine oxidase-xanthine or by c) alcohol oxidase-alcohol or by d) galactose oxidase-galactose.

In place of porcine liver esterase coupled antigen, an alkaline phosphatase coupled antigen and in place of the fluorescein diacetate $10^4$M eosin diphosphate is used. The same result is obtained.

EXAMPLE 6: Enzymatic Immunoassay

Antibody solutions of increasing concentration are adsorbed on to polystyrene wells. An enzyme-coupled antigen is allowed to combine with the antibody for a fixed time. The uncombined antigen is washed out and replaced with a buffered solution of enzyme substrate, the precursor of the photosensitizer, and is incubated for a fixed time. An aliquot of the supernatant of each well is added to a vinyl monomer together with an electron donor and is exposed to a light source. The monomer chosen, namely calcium acrylate, is one which on polymerization produces a light scattering polymer. The amount of scatter in each tube is proportional to the amount of antibody (the analyte). Hence the present system provides a quantitative measure of the analyte. This procedure also permits the assay of labile substances which cannot be conveniently transported, such as might be encountered in tropical countries, since the assay can be divided into two parts, a) the production in the field of a photosensitizer and b) the production of polymer and its quantitatization elsewhere. In the second part prior to the illumination the solution is deoxygenated with nitrogen.

EXAMPLE 7: Enzymatic Immunoassay

In this example, a dehydrogenase enzyme converts NADP to reduced NADP, the later being an electron donor for a photosensitizer.

Glucose-6-phosphate dehydrogenase is coupled to an antibody and the conjugate is allowed to combine with the antigen previously spotted and fixed on a glass slide. Uncombined conjugate is washed off. The slide is dipped into a solution containing 3% methylene bisacrylamide, 0.25% glucose-6-phosphate, 0.1% NADP, 0.05% Eosin and is exposed to a tungsten-iodine lamp with an amber glass filter. A visible white precipitate forms at the site of the antigen.

The amber glass filter is used to eliminate near- ultraviolet light. It is found that reduced NAD and NADP can serve as a photosensitizer as well as an electron donor. These reagents, as well as impurities that absorb near-ultraviolet light, can give false positive results unless near-ultraviolet radiation is removed. Glucose-6-phosphate dehydrogenase can be replaced by any of the dehydrogenases which can reduce NAD or NADP.

EXAMPLE 8: Immunoassay with Analyte Linked to Electron Donor

This is an example of a homogeneous assay according to the method of Carrico in which the analyte is a hapten which competes with a NAD-hapten conjugate for a limited amount of antibody. Only NAD-hapten which is not complexed with antibody is capable of being cycled between two oxidation states. Cycling is achieved by means of a dehydrogenase enzyme. The concentration of analyte in the sample is proportional to the amount of free NAD hapten.

The analyte hapten, NAD-hapten conjugate and a limited amount of antibody are allowed to equilibrate in a glass test tube. Next lactate dehydrogenase, lithium lactate and Methylene Blue dye are added and the test tube exposed to a tungsten lamp with an amber glass filter. Light scatter develops progressively in the liquid volume at a rate proportional to the amount of analyte.

EXAMPLE 9: Homogeneous Enzyme Immunoassay

A. Morris ("Apoenzyme Reactivation Immunoassays Using Flavin Adenine Dinucleotide as Label", *Clinical Immunochemistry: Principles of Methods and Applications*, Eds. R.C. Boguslaski, E.T. Maggio and R.M. Nakamura, pp. 115-130, (1984), Little Brown and Company, Boston/Toronto) developed a homogeneous immunoassay based on the observation that when the prosthetic group of flavin adenine dinucleotide (FAD) of glucose oxidase is covalently bound to another chemical, for example, an antigen, the enzyme in the antigen-antibody complex is inactive. Furthermore, the enzyme can be decomposed under nonphysiological conditions to a prosthetic group of coenzyme and the protein portion or apoenzyme. The separated components are inactive, but on mixing under physiological conditions the two reassociate forming the fully active complete enzyme. The test is performed by mixing the analyte with a known amount of analyte-prosthetic group conjugate and adding apoenzyme. If a small amount of antibody is now added, the amount of active enzyme, that is uncombined with antibody, will be directly proportional to the amount of added test analyte.

Thus a measured amount of FAD conjugated antigen is added to an unknown amount of the antigen which is the analyte. Excess glucose oxidase apoenzyme is added and allowed to combine with the FAD of the FAD conjugated antigen. Next a small amount of antibody is then added and allowed to combine with the FAD conjugated antigen and the test antigen. Detection of complete enzyme [apoenzyme-FAD conjugated antigen] that has not been inactivated by antibody complexation [apoenzyme FAD conjugated antigen-antibody] is performed by addition of 3% methylene bisacrylamide, 5% glucose, 0.001% horseradish peroxidase,0.001% porcine liver esterase 1% triethanolamine, 0.1% cerous chloride and $10^{-4}$M dichlorodiacetylfluorescin. This solution is exposed to a 250 Watt medium pressure mercury lamp filtered with a cobalt blue filter and becomes opaque with the formation of polymethylene bisacrylamide.

B. Example 9A is repeated, but the apoenzyme of xanthine oxidase and xanthine replace the apoenzyme of glucose oxidase and glucose respectively. The same result is observed. Both these enzymes are members of a group of over 40 enzymes identified as flavoprotein enzymes containing either flavin adenine dinucleotide (FAD) or flavin mononucleotide (FMN).

EXAMPLE 10: Enzymatic Nucleic Acid Assay

In this example a specific nucleic acid sequence is detected by an enzymatic assay as in example 4.

A biotinylated nucleic acid probe is allowed to hybridize with its complementary single stranded DNA analyte which is first transferred and immobilized on nitrocellose paper. Following hybridization the uncombined probe is removed by washing. The nitrocellulose paper is then soaked in bovine albumin solution to block non-specific adsorption. Next the nitrocellulose paper is immersed in a solution containing horse radish peroxidase coupled avidin. Following washout of uncombined peroxidase-avidin, the nitrocellulose paper is immersed in a solution containing $10^{-4}$Molar DCDAF, 0.001% esterase enzyme, 0.03% hydrogen peroxide, 15% acrylamide, 0.5% triethanolamine, and 0.05% cerous chloride. Nitrogen gas is bubbled through the solution. On exposure to a 250 Watt medium pressure mercury lamp filtered with a cobalt glass, polyacrylamide deposits at the sites of hybridization. To detect the polymer, the nitrocellulose paper with its sample side down is contacted with a smooth flat layer of whice titanium dioxide pigment powder. Then the paper held vertically is shaken by an acoustical vibrator to which it is clamped. By this means the only pigment particles remaining on the paper are those where the sticky polyacrylamide is present and hence at the sites where the hybridization with its overlying polyacrylamide appears. The paper is then dried, immersed in immersion oil to render the nitrocellulose paper transparent and viewed against black paper. The white titanium dioxide pigment is then apparent at the sites.

EXAMPLE 11: Non-Enzymatic Nucleic Acid Probe

An eosinated nucleic acid probe is made by reaction of eosin isothiocyanate with the ethylene diamine derivative of the nucleic acid probe. This probe is hybridized with complimentary single stranded nucleic acid which has been immobilized on nitrocellulose paper. Following hybridization, the uncombined probe is removed by washing. Next the nitrocellulose paper is soaked in bovine albumin solution to block non-specific adsorption. Following washout of unbound albumin the nitrocellulose paper is immersed in a solution containing 15% acrylamide, 1% methylene bisacrylamide, 0.5% treithanolamine, and the solutions saturated with horse radish peroxidase enzyme. Nitrogen gas is bubbled through the solution. On exposure to a 250 Watt medium pressure mercury lamp with a cobalt blue glass filter polyacrylamide crosslinked with methylene bisacrylamide and containing trapped peroxidase deposits at the sites of hybridization. The unreacted monomer mixture is washed out and replaced with a buffered solution (pH6) containing 0.03% hydrogen peroxide, 4-chloronaphthol. A blue coloration develops at the surface where the polyacrylamide gel is located.

It will, be appreciated that the instant specification and examples are set forth by way of illustration and not limitation, and that various modifications and changes may be made without departing from the spirit and scope of the present invention.

What is claimed is:

1. A diagnostic test composition for detecting and measuring an analyte possessing biologic activity, the composition comprising
  (a) a photocatalyst system capable of converting a monomer to a polymer upon exposure to light, said photocatalyst system operating by free radical polymerization, the photocatalyst system comprising chemical moieties comprising a photosensitizer for photopolymerization and an electron donor, the electron donor being capable of donating electrons only when the photosensitizer is in a light excited state, and 1) said analyte comprising a ligand which either contains at least one of said chemical moieties or is a generator of a least one of said chemical moieties, or 2) in the case that the analyte lacks any photocatalyst property, the analyte is linked by a specific ligand to a generator of at least one of said chemical moieties, said ligand being one member of either an antibody/antigen pair or a hybridization probe/target pair, and
  (b) at least one monomer capable of undergoing addition polymerization, said monomer being selected from the group consisting of acrylamide, N-octyl acrylamide, methacrylamide, N-methylacrylamide, acrylic acid, methacrylic acid, hydroxymethyl acrylamide, methylene bisacrylamide, acrylonitrile, methyl acrylate, ethylene glycol methacrylate, propylene glycol methacrylate, acrylamide propane sulfonic acid, N-(3-aminopropyl)-methacrylamide, pentaerythritoltriacrylate, polyethyleneglycol diacrylate, vinyl pyrrolidine, vinyl pyridine, multivalent salts of acrylic acid, multivalent salts of methacrylic acid and combinations of the aforesaid monomers.

2. A composition according to claim 1, wherein the analyte is a photocatalyst moiety or generator of a photocatalyst moiety.

3. A composition according to claim 1, which is a diagnostic immunoassay test composition wherein said specific ligand is selected from the group consisting of an antibody, an antigen binding segment of an antibody, an antigen and a hapten wherein when the specific ligand is an antibody or an antigen binding segment of an antibody, the analyte is an antigen or a hapten and wherein when the specific ligand is an antigen or a hapten the analyte is an antibody or an antigen binding segment of an antibody.

4. A composition according to claim 1, which is a diagnostic test composition for the assay of a nucleic acid wherein said specific ligand is a hybridizable nucleic acid probe containing a known sequence, said sequence being single stranded and complementary to a single stranded segment of a nucleic acid analyte.

5. A composition according to claim 1, wherein the analyte is linked to a chemical moiety which is an electron donor.

6. A composition according to claim 5, wherein the electron donor is selected from the group consisting of nicotinamide adenine dinucleotide, nicotinamide adenine dinucleotide phosphate, cytochrome C, ferredoxin, riboflavin, flavinadeninedinucleotide, flavinmononucleotide, methyl viologen and derivatives of methyl viologen.

7. A composition according to claim 1, wherein said generator generates an electron donor from precursor.

8. A composition according to claim 7, wherein the generator of the electron donor is an oxidoreductase enzyme.

9. A composition according to claim 8, wherein the oxidoreductase is selected from the group consisting of nicotinamide adenine dinucleotide oxidoreductases, nicotinamide adenine dinucleotide phosphate oxidoreductases, cytochrome oxidoreductases and ferredoxin oxidoreductases.

10. A composition according to claim 8, wherein the oxidoreductase is selected from the group consisting of glucose-6-phosphate dehydrogenase, alcohol dehydrogenase, lactate dehydrogenase and glucose dehydrogenase.

11. A composition according to claim 1, wherein the chemical moiety is a photosensitizer.

12. A composition according to claim 11, wherein the photosensitizer is selected from the group consisting of a flavin, a coumarin, an acridine, a xanthene and a phenothiazine.

13. A composition according to claim 12, wherein the coumarin is selected from the group consisting of amino coumarins and hydroxy coumarins.

14. A composition according to claim 12, wherein the coumarin is selected from the group consisting of 7-amino-4-methyl coumarin, 7-amino-4 trifluoromethyl coumarin, 7-hydroxy-4-methyl coumarin and 7-hydroxy coumarin.

15. A composition according to claim 12, wherein the acridine is selected from the group consisting of monoaminoacridines and diaminoacridines.

16. A composition according to claim 12, wherein the acridine is selected from the group consisting of Acridine Yellow, Coriphosphine O, Acriflavine, Euflavin, Proflavine, Phosphine and Rheonine A.

17. A composition according to claim 12, wherein the xanthene is selected from the group consisting of Fluorescein and Fluorescein derivatives.

18. A composition according to claim 12, wherein the xanthene is selected from the group consisting of Fluorescein, Eosin, dichlorofluorescein, Rose Bengal, dibromo eosin, members of the pyronine family and members of the rhodamine family.

19. A composition according to claim 12, wherein the phenothiazine is selected from the group consisting of monoaminophenothiazines and diaminophenothiazines.

20. A composition according to claim 12, wherein the phenothiazine is selected from the group consisting of Thionine, Azure C, Azure A, Toluidine Blue O, Methylene Blue, New Methylene Blue and Methylene Green.

21. A composition according to claim 1, wherein said generator generates a photosensitizer from a precursor.

22. A composition according to claim 21, wherein the generator of the photosensitizer is selected from the group consisting of a peroxidase, an oxidase and a hydrolase.

23. A composition according to claim 21, wherein said oxidase generates hydrogen peroxide thereby providing an oxidant for peroxidase generation of the photosensitizer.

24. A composition according to claim 22, wherein the oxidase is selected from the group consisting of alcohol oxidase, ascorbate oxidase, choline oxidase, galactose oxidase, glucose oxidase, oxalate oxidase, pyruvate oxidase and xanthine oxidase.

25. A composition according to claim 22, wherein the peroxidase is selected form the group consisting of horseradish peroxidase, myeloperoxidase, thyroid peroxidase, salivary peroxidase, intestinal peroxidase, lactoperoxidase and microperoxidase.

26. A composition according to claim 25, wherein said horseradish peroxidase generates a photosensitizer selected from the group consisting of a reduced xanthene and a reduced phenothiazine.

27. A composition according to claim 26, wherein the reduced xanthene is selected from the group consisting of fluorescin and derivatives of fluorescin.

28. A composition according to claim 26, wherein the reduced xanthene is selected from the group consisting of dichlorofluorescin and dihydroeosin.

29. a composition according to claim 22, wherein the hydrolase is selected from the group consisting of an esterase, a phosphatase, a peptidase, a sulfatase, a glucuronidase and a galactosidase.

30. A composition according to claim 29, wherein the said esterase generates a photosensitizer selected from the group consisting of esters of fluorescein, halogenated derivatives of the esters of fluorescein and esters of 7-hydroxy, coumarin 31. A composition according to claim 29, wherein said phosphatase generates a photosensitizer selected from the group consisting of a diphosphate of Fluoroescein, halogenated derivatives of a diphosphate of Fluorescein and a phosphate of 7-hydroxy coumarin.

32. A composition according to claim 29, wherein said sulfatase generates a photosensitizer selected from the group consisting of Fluorescein disulfate, halogenated derivatives of Fluorescein disulfate and a sulfate of 7-hydroxy coumarin.

33. A composition according to claim 29, wherein said glucuronidase generates a photosensitizer selected from the group consisting of Fluorescein diglucuronide, halogenated derivatives of Fluorescein diglucuronide and a glucuronide of 7-hydroxycoumarin.

34. A composition according to claim 29, wherein said galactoside generates a photosensitizer selected from the group consisting of Fluorescein digalactoside, halogenated derivatives of Fluorescein digalactoside and galastoside of 7-hydroxy coumarin.

35. A composition according to claim 29, wherein said peptidase generates a photosensitizer from a peptide derivative of Thionin or a Thionin derivative.

36. A composition according to claim 1, which further comprises an oxygen buffer.

37. A composition according to claim 36, wherein the oxygen buffer is selected from the group consisting of cobalt chelates and oxidase enzymes.

38. A composition according to claim 37, wherein the cobalt chelate is selected from the group consisting of the cobalt chelates of glycylglycine, histidine, diethylenetriamine, triethylenetetramine and vitamin $B_{12a}$.

39. A composition according to claim 37, wherein the oxidase enzyme is selected from the group consisting of alcohol oxidase, ascorbic acid oxidase, galactose oxidase, glucose oxidase, sarcosine oxidase, pyrurate oxidase, choline oxidase, amino acid oxidase, xanthine oxidase.

40. A composition according to claim 1, wherein the multivalent salts are selected from the group consisting of calcium, barium, strontium, cadmium, neodymium, uranium and europium salts.

* * * * *